United States Patent
Qiu et al.

(10) Patent No.: US 10,580,172 B2
(45) Date of Patent: Mar. 3, 2020

(54) CFD SIMULATION ASSISTED 4D DSA RECONSTRUCTION (71) Applicant: Siemens Healthcare GmbH, Erlangen (DE)

(72) Inventors: Feng Qiu, Pennington, NJ (US); Daphne Yu, Yardley, PA (US); Wei Hong, Skillman, NJ (US); Puneet Sharma, Monmouth Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 176 days.

(21) Appl. No.: 15/745,725

(22) PCT Filed: Sep. 2, 2015

(86) PCT No.: PCT/US2015/048050
§ 371 (c)(1),
(2) Date: Jan. 18, 2018

(87) PCT Pub. No.: WO2017/039646
PCT Pub. Date: Mar. 9, 2017

(65) Prior Publication Data
US 2018/0211422 A1 Jul. 26, 2018

(51) Int. Cl.
*G06T 11/00* (2006.01)
*A61B 6/00* (2006.01)
(Continued)

(52) U.S. Cl.
CPC ............ *G06T 11/008* (2013.01); *A61B 6/466* (2013.01); *A61B 6/487* (2013.01); *A61B 6/504* (2013.01);
(Continued)

(58) Field of Classification Search
CPC ....... A61B 6/507; A61B 6/5217; A61B 6/487; A61B 6/504; A61B 6/5205; A61B 6/5258;
(Continued)

(56) References Cited

U.S. PATENT DOCUMENTS 9,349,178 B1 * 5/2016 Itu ......................... G16H 50/50
9,679,374 B2 * 6/2017 Choi .................. A61B 5/02007
(Continued)

OTHER PUBLICATIONS

International Search Report dated Nov. 29, 2016 in corresponding International Application No. PCT/US2015/048050.
(Continued)

*Primary Examiner* — Pinalben Patel (57) ABSTRACT

A computer-implemented method of reducing 4D Digital Subtracted Angiography (DSA) reconstruction artifacts using a computational fluid dynamics (CFD) simulation includes a computer receiving first DSA time sequence data comprising a representation of a plurality of vessels and segmenting a vessel of interest from the first DSA time sequence data. The computer uses the CFD simulation to simulate fluid dynamics across the vessel of interest to yield a flow field and determines a plurality of simulated time activity curve parameters for each voxel inside the vessel of interest using the flow field. Then, the computer applies a reconstruction process to second DSA time sequence data to yield a DSA volume. This reconstruction process is constrained by the plurality of simulated time activity curve parameters for each voxel inside the vessel of interest.

16 Claims, 5 Drawing Sheets (51) Int. Cl.
    *G06T 5/50* (2006.01)
    *G16H 50/50* (2018.01)
    *G06T 7/00* (2017.01)
(52) U.S. Cl.
    CPC ............ *A61B 6/507* (2013.01); *A61B 6/5205* (2013.01); *A61B 6/5217* (2013.01); *A61B 6/5258* (2013.01); *G06T 5/50* (2013.01); *G06T 7/0016* (2013.01); *G16H 50/50* (2018.01); *G06T 2207/10076* (2013.01); *G06T 2207/30104* (2013.01); *G06T 2211/404* (2013.01)
(58) Field of Classification Search
    CPC ..... A61B 6/466; G06T 11/008; G06T 7/0016; G06T 2211/404; G06T 5/50; G06T 2207/30104; G06T 2207/10076; G16H 50/50
    See application file for complete search history.

(56)  References Cited

U.S. PATENT DOCUMENTS

| | | | | |
|---|---|---|---|---|
| 2012/0041318 A1* | 2/2012 | Taylor | ................ | A61B 5/02007 600/504 |
| 2012/0114217 A1 | 5/2012 | Mistretta et al. | | |
| 2013/0253895 A1* | 9/2013 | Okell | .................... | A61B 6/507 703/11 |
| 2014/0136174 A1* | 5/2014 | Audigier | ............. | G06F 19/3481 703/11 |
| 2015/0213600 A1* | 7/2015 | Kyriakou | ............... | A61B 6/032 345/424 |
| 2015/0282765 A1* | 10/2015 | Goshen | .................. | A61B 6/032 600/408 |
| 2015/0339847 A1* | 11/2015 | Benishti | ................. | G16H 50/30 382/131 |
| 2015/0351714 A1* | 12/2015 | De Backer | ............. | G16H 50/50 600/427 |
| 2016/0066794 A1* | 3/2016 | Klinder | .................. | G16H 50/50 600/424 |
| 2017/0068796 A1* | 3/2017 | Passerini | ............. | G06F 17/5009 |
| 2018/0206808 A1* | 7/2018 | Grass | ..................... | A61B 6/032 |
| 2018/0218521 A1* | 8/2018 | Kowarschik | .......... | G06T 11/008 |

OTHER PUBLICATIONS

Claus Bernhard E et al: "Circular 1-20 tomosynthesis for neuro perfusion imaging on an interventional C-arm", Progress in Biomedical Optics and Imaging, SPIE—International Society for Optical Engineering, Bellingham, WA, US, vol. 9412, Mar. 18, 2015 (Mar. 18, 2015), pp. 94122A-1-94122A-9.

* cited by examiner

CFD SIMULATION ASSISTED 4D DSA RECONSTRUCTION

TECHNICAL FIELD

The present disclosure relates generally to methods, systems, and apparatuses for reducing 4D Digital Subtracted Angiography (DSA) reconstruction artifacts using a computational fluid dynamics (CFD) simulation. The proposed technology may be applied, for example, to enhance vessel tracking and visualization in angiography applications.

BACKGROUND

4D Digital Subtracted Angiography (DSA) is a sequence of reconstructed 3D angiography images over time, representing blood flow information, typically within the head. The subtraction of the flow image from a baseline image removes the static anatomy such as the skull, leaving only the flow information. In conventional systems, due to scanner limitations, the 3D volume of each 4D DSA time step is reconstructed from a limited number of scanner images projected from a narrow range of projection angles. On these images, multiple vessel branches at different depth might be projected onto the same region. The overlapping vessel branches result in reconstruction artifacts (e.g., blood flowing from minor branches to a major artery). Accordingly, it is desired to provide a technique for reducing these artifacts to produce a higher-quality image.

SUMMARY

Embodiments of the present invention address and overcome one or more of the above shortcomings and drawbacks, by providing methods, systems, and apparatuses related to reducing 4D Digital Subtracted Angiography (DSA) reconstruction artifacts using a computational fluid dynamics (CFD) simulation.

According to some embodiments, a computer-implemented method of reducing 4D DSA reconstruction artifacts using a CFD simulation includes a computer receiving first DSA time sequence data comprising a representation of vessels and segmenting a vessel of interest from the first DSA time sequence data. The computer uses the CFD simulation to simulate fluid dynamics across the vessel of interest to yield a flow field and determines simulated time activity curve parameters for each voxel inside the vessel of interest using the flow field. Then, the computer applies a reconstruction process to second DSA time sequence data to yield a DSA volume. This reconstruction process is constrained by the simulated time activity curve parameters for each voxel inside the vessel of interest. In some embodiments, the method further includes the computer computing non-simulated time activity curve parameters from the DSA volume and generating a three-dimensional visualization of differences between the simulated time activity curve parameters and the non-simulated time activity curve parameters.

In some embodiments, the aforementioned method includes various additional features which enhance, refine, or otherwise modify the method. For example, in some embodiments, the CFD simulation is executed with a boundary condition defined by reconstructing a first DSA volume based on the first DSA time sequence data, identifying one or more locations in the DSA volume without overlapping vessels, and comparing one or more time-density curves at the one or more locations to the DSA volume to define the boundary condition. In other embodiments, the CFD simulation utilizes a reduced-order model that defines cross-sections across the vessel of interest and performs averaging across each of the cross-sections to solve for flow-rate.

Various techniques may be used for determining the simulated time activity curve parameters for each voxel inside the vessel of interest. For example, in one embodiment, these parameters are determined by first computing simulated 4D volumes from the flow field. Each of these simulated 4D volumes simulates density of flow in the vessel of interest over time. Then, the simulated 4D volumes are used to determine the simulated time activity curve parameters for each voxel inside the vessel of interest. Once determined, the simulated time activity curve parameters may be used to conditionally implement back-projection during the reconstruction process. The exact implementation will vary according to the exact parameters used.

In some embodiments of the aforementioned method, the simulated time activity curve parameters for a respective voxel comprise a time-of-arrival parameter representative of a length of time that the voxel is at a predetermined percentage of maximum contrast. In these embodiments, the reconstruction process may conditionally reconstruct each respective voxel in the DSA volume by computing a difference between the time of arrival parameter of the respective voxel and acquisition time of the second DSA time sequence data. If the difference is less than a threshold value, the second DSA time sequence data is back-projected to the respective voxel.

In some embodiments of the aforementioned method, the simulated time activity curve parameters for a respective voxel comprise a maximum contrast time parameter representative of a length of time that the respective voxel is at maximum contrast. In these embodiments, the reconstruction process may conditionally reconstruct each respective voxel in the DSA volume by computing a difference between the maximum contrast time parameter of the respective voxel and acquisition time of the second DSA time sequence data. Then, if the difference is less than a threshold value, the second DSA time sequence data can be back-projected to the respective voxel.

In some embodiments of the aforementioned method, the simulated time activity curve parameters for a respective voxel comprise a contrast intensity parameter representative of density in the respective voxel over time. In these embodiments, the reconstruction process may conditionally reconstruct each respective voxel in the DSA volume by computing a difference between the contrast intensity parameter of the respective voxel and contrast intensity of a pixel in the second DSA time sequence data. If the difference is less than a threshold value, the second DSA time sequence data is projected to the respective voxel.

According to other embodiments of the present invention, an article of manufacture for reducing 4D DSA reconstruction artifacts using a CFD simulation includes a non-transitory, tangible computer-readable medium holding computer-executable instructions for performing the aforementioned method, with or without the additional features discussed above.

According to other embodiments, a system for reducing DSA reconstruction artifacts using a CFD simulation comprises a simulation interface, a segmentation component, a CFD simulation component, and a reconstruction component. The scanner interface is configured to (i) receive first DSA time sequence data from a DSA scanner, the first DSA time sequence data comprising a first representation of vessels and (ii) receive second DSA time sequence data from the DSA scanner, the second DSA time sequence data comprising a second representation of the vessels. The segmentation component segments a vessel of interest from the first DSA time sequence data. The CFD simulation component simulates fluid dynamics across the vessel of interest to yield a flow field, and determines simulated time activity curve parameters for each voxel inside the vessel of interest using the flow field. The reconstruction component performs a reconstruction process on a second DSA time sequence data to yield a DSA volume. This reconstruction process is constrained by the simulated time activity curve parameters for each voxel inside the vessel of interest.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The following disclosure describes several embodiments directed at methods, systems, and apparatuses related to reducing 4D Digital Subtracted Angiography (DSA) reconstruction artifacts using a computational fluid dynamics (CFD) simulation. More specifically, using the techniques described herein, various parameters resulting from CFD simulation(s) and 4D DSA projection images (e.g., TOA, contrast intensity function, etc.) are compared and analyzed to detect reconstruction artifacts. The differences between individual parameter values are used as the probability or reliability to improve the reconstruction quality.

Figure 1:
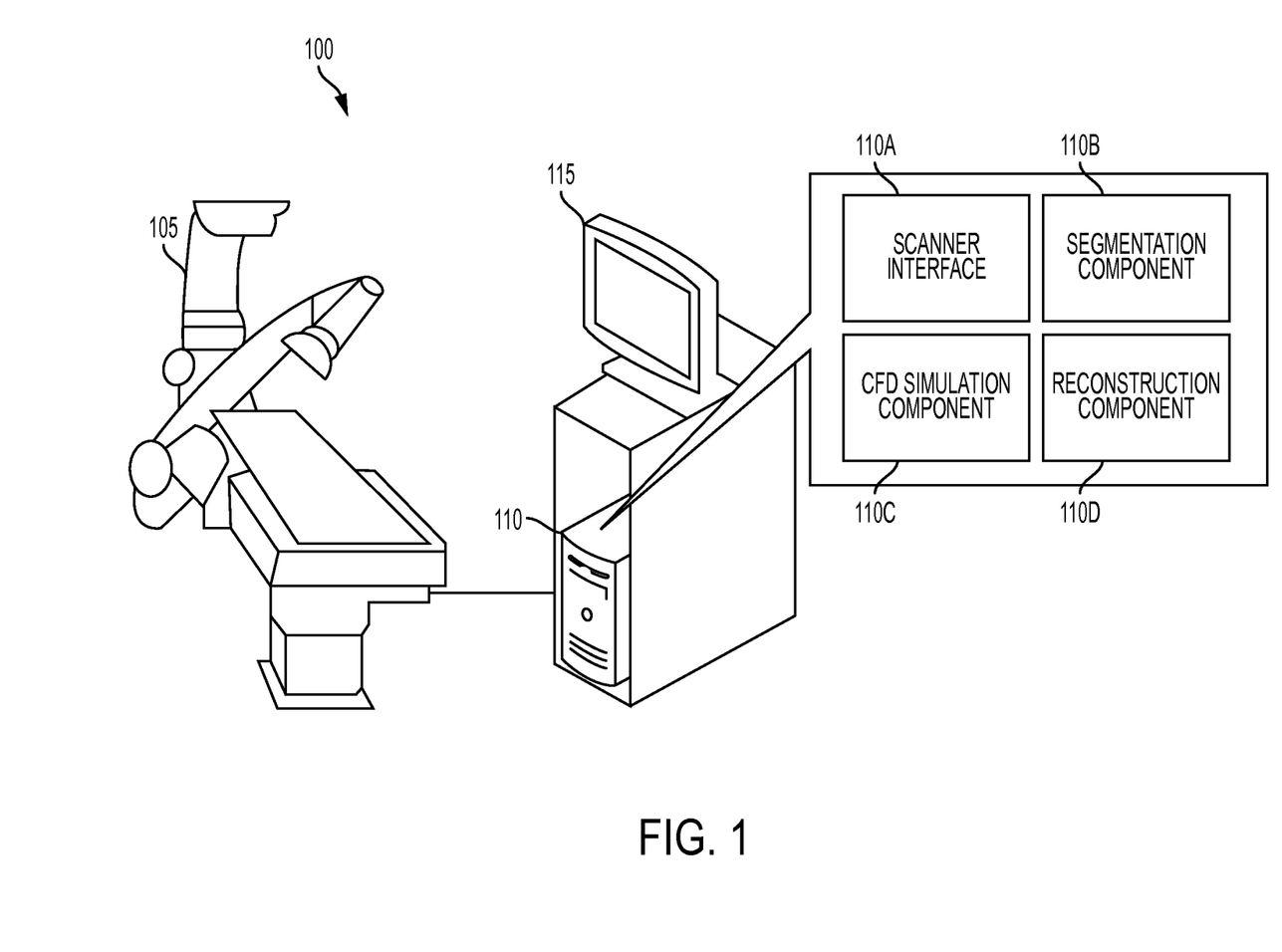
FIG. 1 provides an overview of a system, according to some embodiments.

FIG. 1 provides an overview of a system 100, according to some embodiments. The system 100 includes an X-ray Imaging Device 105 for acquiring DSA images. As is known in the art, DSA includes acquisition of a "mask image" of a region of interest prior to introducing contrast media into the region of interest. The mask image represents background anatomic detail, and is subtracted from subsequently-acquired contrast media-enhanced images in order to remove the background anatomic detail from these images. Devices for acquiring DSA images are generally known in the art and, thus, only briefly described herein. Briefly, the X-ray Imaging Device includes a C-arm on which an X-ray radiation source and a radiation detector are mounted. A patient lies on a table between the X-ray radiation source and the radiation detector. The C-arm rotates around the patient to acquire x-ray images. It should be noted that the representation of the X-ray Imaging Device 105 is merely for illustration purposes. In other embodiments, the X-ray Imaging Device 105 may include additional components found in conventional systems but not shown in FIG. 1.

An Imaging Computer 110 includes a Scanner Interface 110A for receiving DSA time sequence data from the X-ray Imaging Device 105. A Segmentation Component 110B within the Imaging Computer 110 segments a vessel of interest from the DSA time sequence data. The segmentation may be performed using any technique generally known in the art. For example, in some embodiments, the segmentation is automatically performed by thresholding the data based on a predetermined intensity range and applying an iso-surface extraction of the surface boundary. In other embodiments, other automatic segmentation techniques may be used or, alternatively, manual or semi-automatic techniques.

Continuing with reference to FIG. 1, a CFD Simulation Component 110C simulates fluid dynamics across the vessel of interest. As is generally understood in the art, CFD is a branch of fluid mechanics that uses numerical methods and mathematical modeling to solve and analyze problems involving fluid flows. The CFD simulation results in a flow field which, in turn, is used by the CFD Simulation Component 110C to determine one or more simulated time activity curve parameters for each voxel inside the vessel of interest.

Various types of CFD simulations generally known in the art may be used by the CFD Simulation Component 110C. For example, in one embodiment, a 3D+time unsteady flow computation is used, wherein the velocity in each of the 3 directions is explicitly solved for in the 3D domain (i.e. the 3D model of the vascular structure), without making any assumptions on the shape of the flow profile. In another embodiment, reduced-order models (e.g., a Quasi 1-D model) may be used, wherein the geometry of the vascular structure is defined by a centerline and an effective radius associated to each point on the centerline. In such a domain, the 3D Navier-Stokes equations can then be simplified by performing averaging across each cross-section and solving for the flow-rate (Q), instead of the individual velocity vectors. Assumptions on the shape of the flow profile at each cross-section, such as a parabolic shape or a power-law shape, may be used in the computation. One advantage of performing such reduced-order flow computations is the small computation time it takes to solve such equations, thereby making it possible to use it in real-time. Examples of reduced-order models for flow computation are described in U.S. patent application Ser. No. 13/672,781 entitled "Method and System for Multi-Scale Anatomical and Functional Modeling of Coronary Circulation," and U.S. patent application Ser. No. 14/384,547 entitled "Framework for personalization of coronary flow computations during rest and hyperemia." The entirety of both these applications is incorporated herein by reference. In another embodiment, a machine-learning based flow computation may be used by the CFD Simulation Component 110C, wherein features are extracted from the geometry of the vascular structure, and subsequently fed to a pre-trained machine learning model to compute the flow field. Example techniques for performing a machine-learning based flow computation are described in U.S. patent application Ser. No. 14/516,163 entitled "Method and system for machine learning based assessment of fractional flow reserve," the entirety of which is incorporated herein by reference. The CFD Simulation Component 110C may use various techniques for minimizing computing time (e.g., hardware optimizations, vectorization, and parallelization techniques).

A Reconstruction Component 110D performs a reconstruction process on new DSA time sequence data to yield a DSA volume. To reduce artifacts in the reconstructed data, the reconstruction process is constrained by the simulated time activity curve parameters determined by the CFD Simulation Component 110C. Techniques for applying this constraint are discussed below with reference to FIGS. 2-4. Based on the results of the reconstruction, an image of the vessel can presented on Display 115 (e.g., during a surgical procedure).

Although FIG. 1 only illustrates a single imaging computer, in other embodiments, multiple imaging computers may be used. Collectively, the one or more imaging computers provide functionality for viewing, manipulating, communicating and storing medical images on computer readable media. Example implementations of computers that may be used as the imaging computer 110 are described below with reference to FIG. 5. Additionally, in some embodiments, the Imaging Computer 110 includes a graphical processing unit (GPU) or other hardware that facilitates the parallelization of CFD computations and other computations performed by the Imaging Computer 110.

Figure 2:
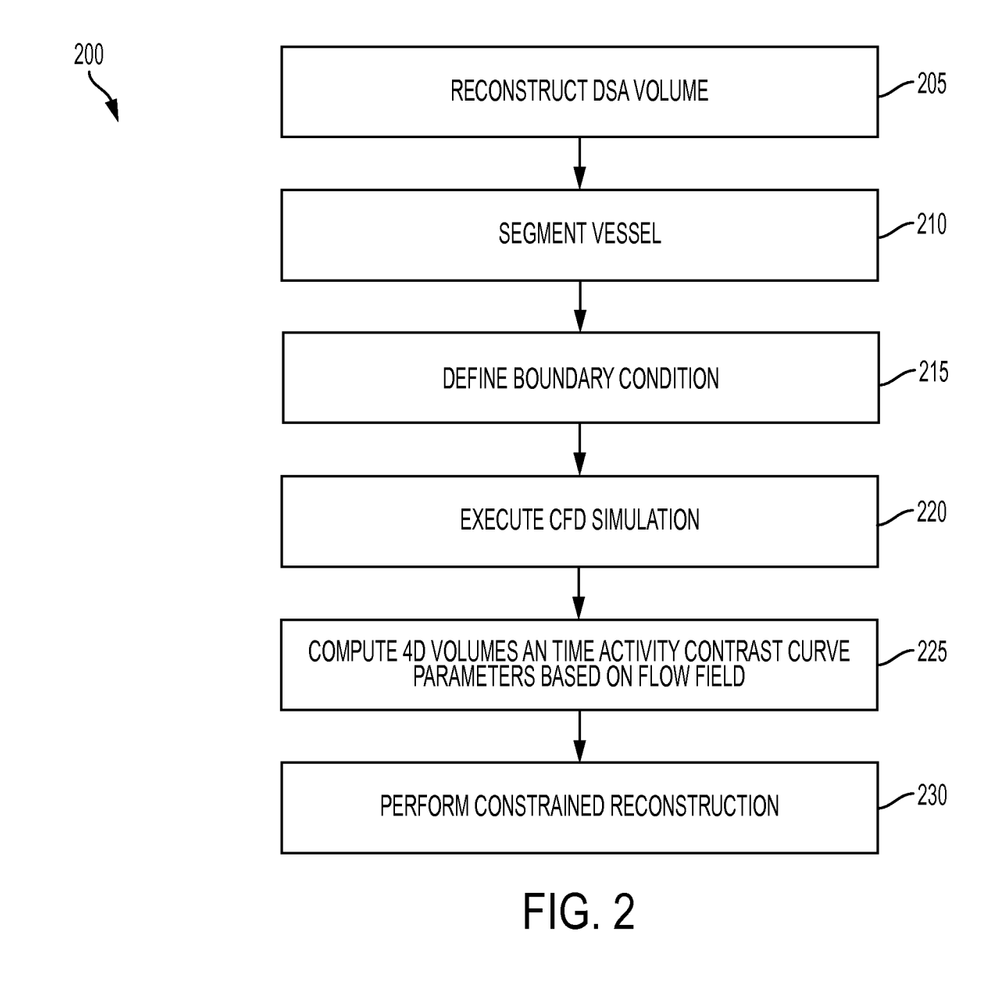
FIG. 2 provides a flow chart showing a process that may be used to reduce the 4D DSA reconstruction artifacts, according to some embodiments of the present invention.

FIG. 2 provides a flow chart showing a process 200 that may be used to reduce the 4D DSA reconstruction artifacts, according to some embodiments of the present invention. Starting at step 205, a DSA volume containing the entire 3D vessel structure is reconstructed from the 4D DSA time sequence, or from another scanning of the same patient (e.g. a registered 3D DSA sequence). Then, at step 210, the vessel that will be used for the CFD simulation is segmented from the DSA volume. This segmentation may be automatic or user controlled. Since the volume is already subtracted, in some embodiments, the segmentation performed at step 210 may be a simple intensity range based thresholding, followed an iso-surface extraction of the surface boundary. This extraction may be performed using any technique generally known in the art.

Next, at step 215, a boundary condition of the CFD simulation is defined. Examples of boundary conditions that may be defined at step 215 include, without limitation, blood flow inlet velocity, contrast agent injection time, position, speed and density, heart beating cycle, etc. Various techniques may be used for estimating the parameters of the defined boundary condition. For example, in some embodiments the boundary conditions are estimated from the 4D DSA images (e.g., based on individual pixel values). Alternatively, in other embodiments, the parameters of the boundary condition may be measured from medical instruments or predefined by the scan protocol used to acquire the 4D DSA data. If there are multiple possible values for the parameters, a set of boundary conditions can be defined for combinations of different values. In some embodiments, the boundary conditions used in the CFD computation are optimized by comparing the time-density curves from CFD to the real data at certain locations that are reliable (e.g., locations where there is no overlap in vessel position).

Continuing with reference to FIG. 2, at step 220, the CFD simulation is executed on the segmented vessel using the boundary condition defined at step 215. In embodiments where a set of boundary conditions is defined, the CFD simulation is run on each combination of boundary conditions. The computations performed by the CFD simulation may be performed in any of a number of different ways as described above with reference to FIG. 1. A flow field is generated as the output of the CFD simulation result.

Figure 3:
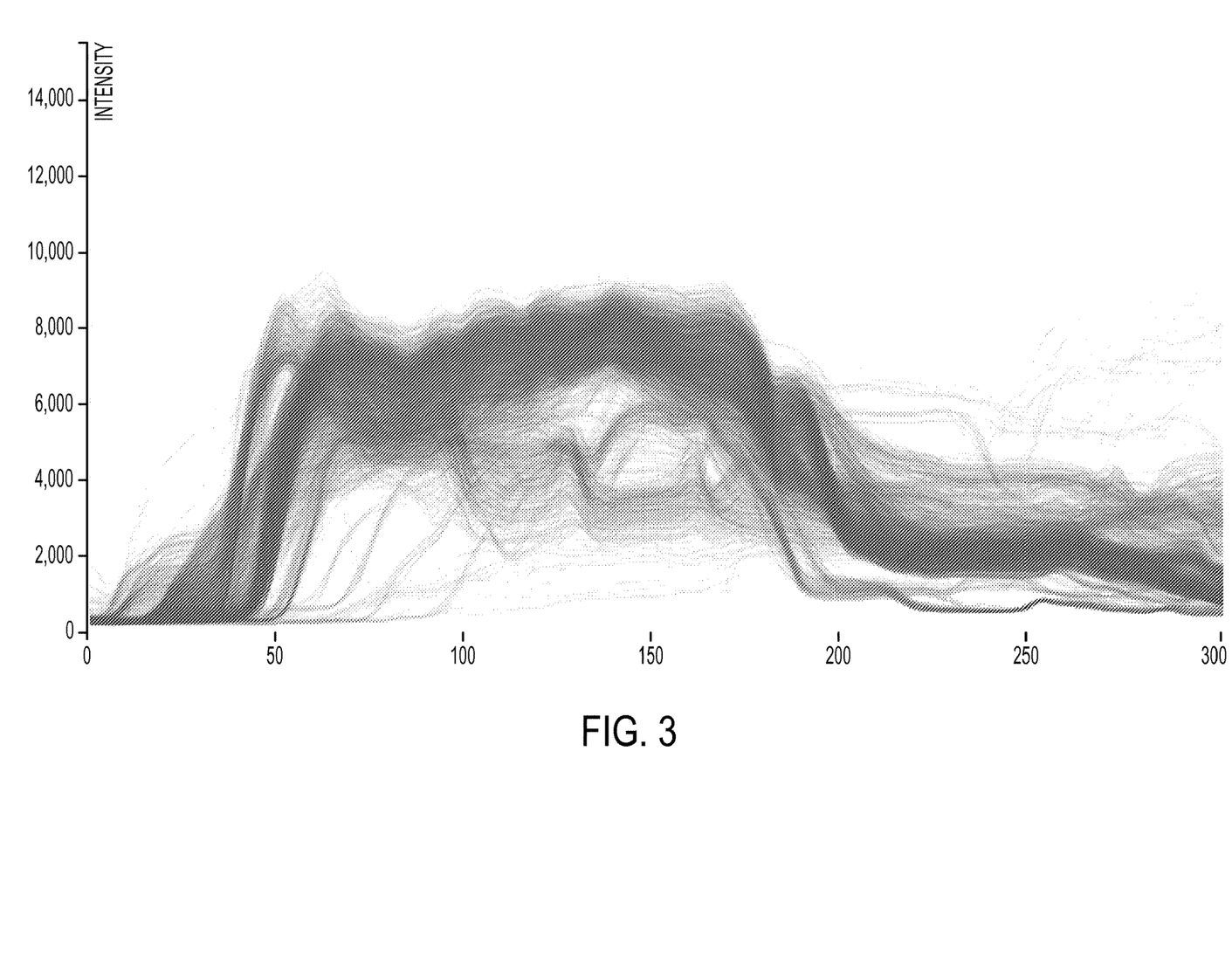
FIG. 3 shows an example voxel intensity curve.

Next, at 225, based on this flow field, a new set of 4D volumes are computed, thereby simulating the density of flow over time. From the set of simulated 4D volumes, the time activity contrast curve parameters for each voxel inside the vessel may be computed. Example time activity contrast curve parameters include, without limitation, time-of-arrival (TOA) as the time at $k_1$ percentage of the maximum contrast, a typical $k_1$ value used is 0.25; maximum contrast time (TOM) as the time of maximum contrast; and contrast intensity (CI) as density over a function of time. FIG. 3 shows an example voxel intensity curve that may result from step 225. In this figure, the x-axis represents time and the y-represents intensity values. The unit for intensity is the real world CT value unit (e.g. Hounsfield value).

Returning to FIG. 2, at step 230, the CFD simulation results are used to correct or reduce the reconstruction artifacts in reconstructing the 4D DSA time sequence. More specifically, the CFD simulation results can be used as an extra constraint on the 4D DSA reconstruction, which requires that the reconstruction results should not be far from the CFD simulation results. For example, one method for tomography reconstruction is back-projection (or filtered back-projection). Traditionally, in this method, a pixel on the projection image is back-projected to the 3D volume and every voxel on the projection ray is updated by the value of the pixel. However, with the CFD simulation results, not every voxel on the ray is back-projected. Instead, constraints and rules can be applied to determine if each voxel along the projection ray will be assigned the pixel value. For example, using blood flow information, the time between the simulated TOA and the TOM to the acquisition time of the projection image (normalization may be necessary) may be compared. If the simulated TOA or TOM of a particular voxel is far from the project image acquisition time, then the voxel will not be assigned with the project image pixel value. As another example, if the difference between the simulated Contrast Intensity (CI) of a voxel and its pixel value is greater than a threshold value, then the back-projection on the voxel will be ignored. Additionally (or alternatively), the difference between the projection pixel value and the simulated CI may be evaluated as the probability or reliability of back-projection on the voxel. It may then be used as a weight to decide whether the voxel should be back-projected or to modulate the back-projection value.

Figure 4:
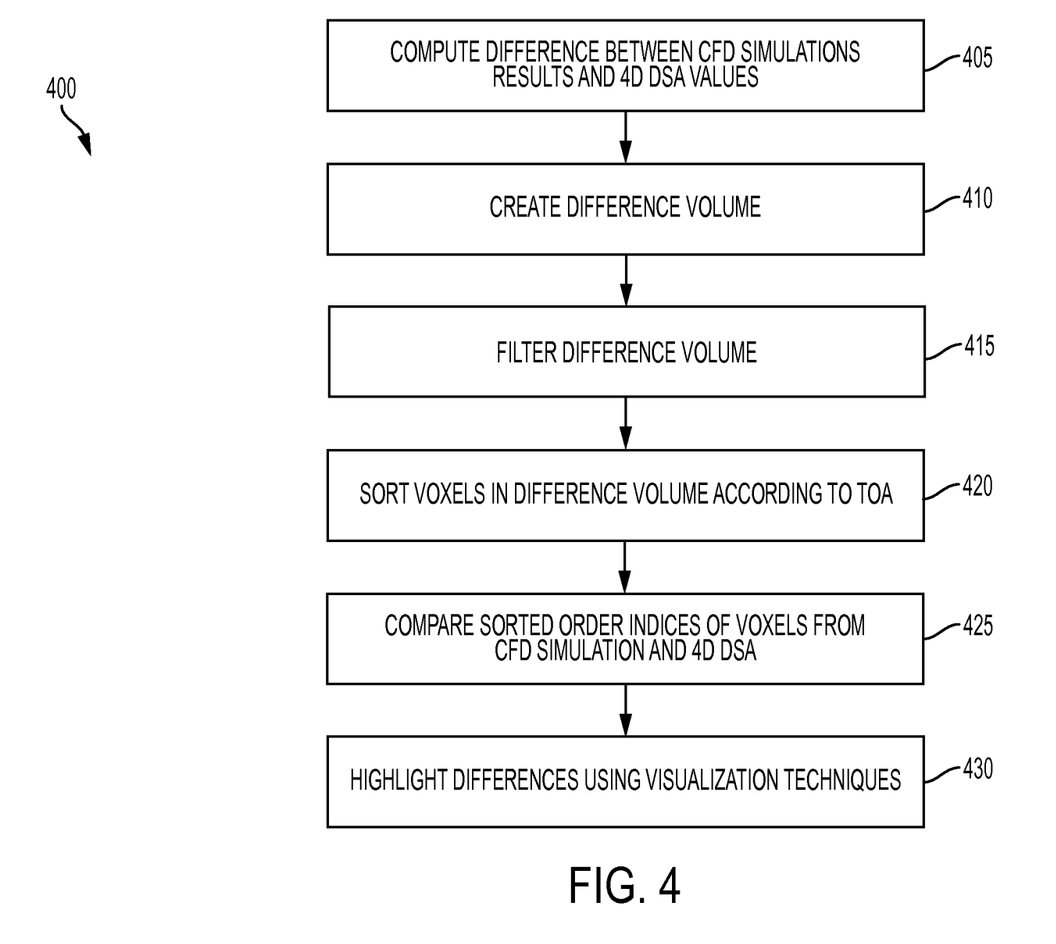
FIG. 4 shows a flow chart illustrating a process for performing this visualization, according to some embodiments.

To further assess any additional artifacts from the reconstructed 4D DSA volumes, one can compute time activity contrast curve parameter (TOA, TOM) volumes from reconstructed 4D DSA time sequence. The assessment can be achieved through the visualization of the difference between the simulated and computed TOA and TOM volumes. FIG. 4 shows a flow chart 400 illustrating a process for performing this visualization, according to some embodiments. Starting at step 405, the difference of one or more parameters (e.g., TOA, TOM, etc.) between the CFD simulation results and 4D DSA values is computed. Next, at step 410, a difference value volume is created and rendered with volume rendering algorithm, which helps the user to identify the regions of large difference values. In some embodiments, the user can also define a threshold and if the difference is larger than the threshold, it can be classified as a reconstruction artifact.

Continuing with reference to FIG. 4, at step 415, the difference values in the difference volume(s) are filtered in a small neighborhood to reduce the noise in computation and reconstruction. The TOA parameter reveals the information of the order of the blood flow arriving at different regions of the vessel. Using this information, at step 420, the voxels are sorted inside the vessel according to the TOA parameter. Then, at step 425, the sorted order indices of voxels from CFD simulation and the 4D DSA data are compared. Next, at step 430, the difference of the sorted order are detected and highlighted with visualization techniques generally known in the art (e.g. coloring voxels of large difference). In some embodiments, the voxels can be grouped into subvolumes (e.g., 2×2×2 or 4×4×4 regions) to simplify the comparison. Also, the voxels can be aligned with the vessel centerline, then the average TOA for the centerline vertices may be computed, and the comparison may be applied on the centerline. If the difference is larger than a certain user defined threshold, it can be classified as reconstruction artifact.

If multiple CFD simulation running cases are available, a pairwise comparison between it and the 4D DSA as discussed above may be applied. This produces a set of difference values for each voxel. Then, statistical analysis can be applied for analysis. For example, this analysis may compute the probability that the TOA or Tmax 0.1 s (or 2 time steps) slower in 4D DSA than in the CFD simulation. If the probability is larger than 50% (or any user defined threshold), it can be classified as reconstruction artifact.

Figure 5:
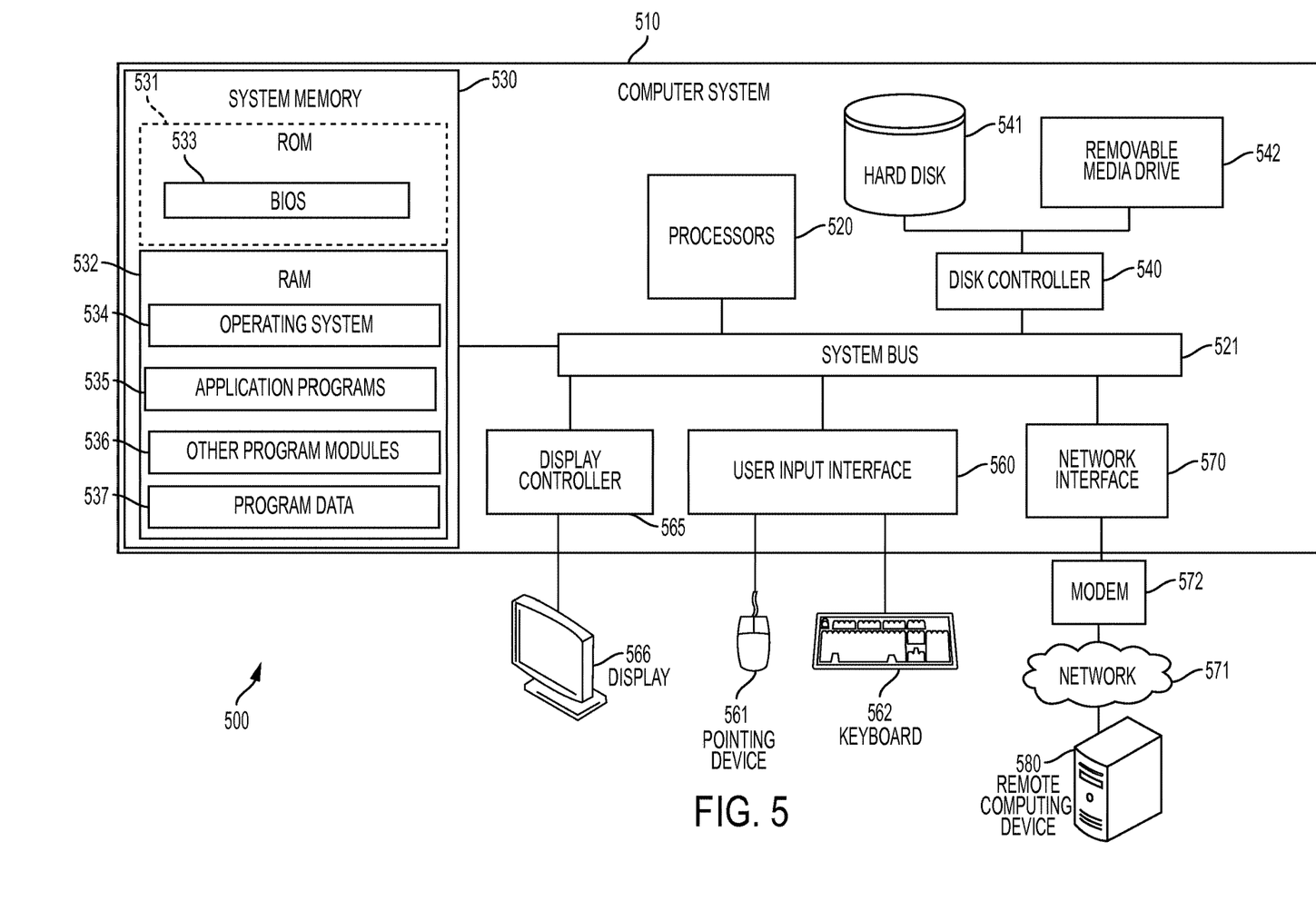
FIG. 5 illustrates an exemplary computing environment within which embodiments of the invention may be implemented.

FIG. 5 illustrates an exemplary computing environment 500 within which embodiments of the invention may be implemented. For example, this computing environment 500 may be used to implement one or more of devices shown in FIG. 1 and execute the processes described herein with reference to FIGS. 2 and 4. The computing environment 500 may include computer system 510, which is one example of a computing system upon which embodiments of the invention may be implemented. Computers and computing environments, such as computer system 510 and computing environment 500, are known to those of skill in the art and thus are described briefly here.

As shown in FIG. 5, the computer system 510 may include a communication mechanism such as a bus 521 or other communication mechanisms for communicating information within the computer system 510. The computer system 510 further includes one or more processors 520 coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system 533 (BIOS) containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processor 520. The pointing device 561, for example, may be a mouse, a trackball, or a pointing stick for communicating direction information and command selections to the processor 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computer 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method of reducing 4D Digital Subtracted Angiography (DSA) reconstruction artifacts using a computational fluid dynamics (CFD) simulation, the method comprising:
   receiving, by a computer, first DSA time sequence data comprising a representation of a plurality of vessels;
   segmenting, by the computer, a vessel of interest from the first DSA time sequence data;
   using, by the computer, the CFD simulation to simulate fluid dynamics across the vessel of interest to yield a flow field;
   determining, by the computer, a plurality of simulated time activity curve parameters for each voxel inside the vessel of interest using the flow field, wherein the plurality of simulated time activity curve parameters for each voxel inside the vessel of interest comprise a time-of-arrival parameter representative of a length of time that the voxel is at a predetermined percentage of maximum contrast; and
   applying, by the computer, a reconstruction process to second DSA time sequence data to yield a DSA volume, wherein the reconstruction process is constrained by the plurality of simulated time activity curve parameters for each voxel inside the vessel of interest and the reconstruction process conditionally reconstructs each voxel in the DSA volume by:
      computing a difference between the time of arrival parameter of the voxel and acquisition time of the second DSA time sequence data; and
      if the difference is less than a threshold value, back-projecting the second DSA time sequence data to the voxel.

2. The method of claim 1, wherein the CFD simulation is executed with a boundary condition is defined by a process comprising:

reconstructing a first DSA volume based on the first DSA time sequence data;
identifying one or more locations in the first DSA volume without overlapping vessels; and
comparing one or more time-density curves at the one or more locations to the DSA volume to define the boundary condition.

3. The method of claim 1, wherein the CFD simulation comprises computation of unsteady flow in three-dimensions and time across the vessel of interest.

4. The method of claim 1, wherein the CFD simulation utilizes a reduced-order model that defines a plurality of cross-sections across the vessel of interest and performs averaging across each of the plurality of cross-sections to solve for flow-rate.

5. The method of claim 1, wherein the plurality of simulated time activity curve parameters for each voxel inside the vessel of interest are determined using the flow field by:
computing a plurality of simulated 4D volumes from the flow field, wherein each of the plurality of simulated 4D volumes simulates density of flow in the vessel of interest over time; and
using the plurality of simulated 4D volumes to determine the plurality of simulated time activity curve parameters for each voxel inside the vessel of interest.

6. The method of claim 1, wherein the plurality of simulated time activity curve parameters for each voxel comprise a maximum contrast time parameter representative of a length of time that the voxel is at maximum contrast.

7. The method of claim 6, wherein the reconstruction process conditionally reconstructs each voxel in the DSA volume by:
computing a difference between the maximum contrast time parameter of the voxel and acquisition time of the second DSA time sequence data; and
if the difference is less than a threshold value, back-projecting the second DSA time sequence data to the voxel.

8. The method of claim 1, wherein the plurality of simulated time activity curve parameters for a each voxel comprise a contrast intensity parameter representative of density in respective voxel over time.

9. The method of claim 8, wherein the reconstruction process conditionally reconstructs each voxel in the DSA volume by:
computing a difference between the contrast intensity parameter of the voxel and contrast intensity of a pixel in the second DSA time sequence data; and
if the difference is less than a threshold value, back-projecting the second DSA time sequence data to the voxel.

10. The method of claim 1, further comprising:
computing, by the computer, a plurality of non-simulated time activity curve parameters from the DSA volume;
generating, by the computer, a three-dimensional visualization of differences between the plurality of simulated time activity curve parameters and the plurality of non-simulated time activity curve parameters.

11. A method for reducing 4D Digital Subtracted Angiography (DSA) reconstruction artifacts using a computational fluid dynamics (CFD) simulation, the method comprising:
receiving first DSA time sequence data comprising a representation of a plurality of vessels;
segmenting a vessel of interest from the first DSA time sequence data;

using the CFD simulation to simulate fluid dynamics across the vessel of interest to yield a flow field;
determine a plurality of simulated time activity curve parameters for each voxel inside the vessel of interest using the flow field, wherein the plurality of simulated time activity curve parameters for each voxel comprise a maximum contrast time parameter representative of a length of time that the voxel is at maximum contrast; and
applying a reconstruction process to second DSA time sequence data to yield a DSA volume, wherein the reconstruction process is constrained by the plurality of simulated time activity curve parameters for each voxel inside the vessel of interest and wherein the reconstruction process conditionally reconstructs each voxel in the DSA volume by:
computing a difference between the maximum contrast time parameter of the voxel and acquisition time of the second DSA time sequence data; and
if the difference is less than a threshold value, back-projecting the second DSA time sequence data to the voxel.

12. The method of claim 11, wherein the plurality of simulated time activity curve parameters for a each voxel comprise a time-of-arrival parameter representative of a length of time that the voxel is at a predetermined percentage of maximum contrast.

13. The method of claim 12, wherein the reconstruction process conditionally reconstructs each voxel in the DSA volume by:
computing a difference between the time of arrival parameter of the voxel and acquisition time of the second DSA time sequence data; and
if the difference is less than a threshold value, back-projecting the second DSA time sequence data to the voxel.

14. The method of claim 11, wherein the plurality of simulated time activity curve parameters for a each voxel comprise a contrast intensity parameter representative of density in the voxel over time.

15. The method of claim 14, wherein the reconstruction process conditionally reconstructs each voxel in the DSA volume by:
computing a difference between the contrast intensity parameter of the voxel and contrast intensity of a pixel in the second DSA time sequence data; and
if the difference is less than a threshold value, back-projecting the second DSA time sequence data to the voxel.

16. A system for reducing Digital Subtracted Angiography (DSA) reconstruction artifacts using a computational fluid dynamics (CFD) simulation, the system comprising:
a scanner interface configured to:
receive first DSA time sequence data from a DSA scanner, the first DSA time sequence data comprising a first representation of a plurality of vessels,
receive second DSA time sequence data from the DSA scanner, the second DSA time sequence data comprising a second representation of the plurality of vessels;
a segmentation component configured to segment a vessel of interest from the first DSA time sequence data;
a CFD simulation component configured to:
simulate fluid dynamics across the vessel of interest to yield a flow field, and
determine a plurality of simulated time activity curve parameters for each voxel inside the vessel of interest using the flow field, wherein the plurality of simulated time activity curve parameters for each voxel inside the vessel of interest comprise a time-of-arrival parameter representative of a length of time that the voxel is at a predetermined percentage of maximum contrast; and a reconstruction component configured to perform a reconstruction process on second DSA time sequence data to yield a DSA volume, wherein the reconstruction process is constrained by the plurality of simulated time activity curve parameters for each voxel inside the vessel of interest and the reconstruction process conditionally reconstructs each voxel in the DSA volume by:

computing a difference between the time of arrival parameter of the voxel and acquisition time of the second DSA time sequence data; and if the difference is less than a threshold value, back-projecting the second DSA time sequence data to the voxel.

* * * * *